US006692453B2

(12) United States Patent
Wolfe

(10) Patent No.: US 6,692,453 B2
(45) Date of Patent: Feb. 17, 2004

(54) TWO PIECE WRIST-HAND-FINGER ORTHOSIS

(75) Inventor: Andrew W. Wolfe, Omaha, NE (US)

(73) Assignee: Board of Regents, University of Nebraska Medical Center, Omaha, NE (US)

(*) Notice: Subject to any disclaimer, the term of this patent is extended or adjusted under 35 U.S.C. 154(b) by 0 days.

(21) Appl. No.: 10/052,930

(22) Filed: Oct. 22, 2001

(65) Prior Publication Data

US 2003/0078530 A1 Apr. 24, 2003

(51) Int. Cl.⁷ .............................. A61F 5/00; A61F 5/37
(52) U.S. Cl. .............................. 602/21; 602/5; 128/878
(58) Field of Search ..................... 602/5, 6, 12, 20, 602/21; 128/878; 2/16, 20

(56) References Cited

U.S. PATENT DOCUMENTS

| 4,554,912 A | 11/1985 | Haberman |
| 4,672,955 A | 6/1987 | Cooper |
| 4,960,114 A | 10/1990 | Dale |
| 5,219,323 A * | 6/1993 | Singer et al. ............. 601/33 |
| 5,269,748 A | 12/1993 | Lonardo |
| 5,279,545 A * | 1/1994 | Reese, Sr. .................. 602/21 |
| 5,358,471 A * | 10/1994 | Klotz ........................... 602/16 |
| 5,797,803 A * | 8/1998 | Jung ............................ 473/213 |
| 5,891,068 A | 4/1999 | Kenney |
| 6,142,966 A | 11/2000 | Hely |
| 6,179,799 B1 * | 1/2001 | Doran ........................... 602/20 |
| 6,293,918 B1 * | 9/2001 | Wang ........................... 128/878 |

OTHER PUBLICATIONS

Restorative Care of America Inc., 1997–1998 Product Catalog (1996).
Restorative Care of America Inc., Dorsal Resting Hand Orthosis (exact advertisement publishing date unknown; approximately 1997).

* cited by examiner

Primary Examiner—Michael A. Brown
Assistant Examiner—Fenn C Mathew
(74) Attorney, Agent, or Firm—Stinson Morrison Hecker LLP; Nancy T. Morris

(57) ABSTRACT

A two-piece wrist-hand-finger orthosis of the present invention includes a rigid forearm section secured to the patient's arm, and a rigid hand section with a proximally projecting extension lever. The hand section is donned on the patient with the patient's hand in flexion. The hand section is then leveraged into a position of predetermined flexion or extension by pivoting the extension lever downwardly into contact with the forearm section. The extension lever is then secured to the forearm section.

17 Claims, 2 Drawing Sheets

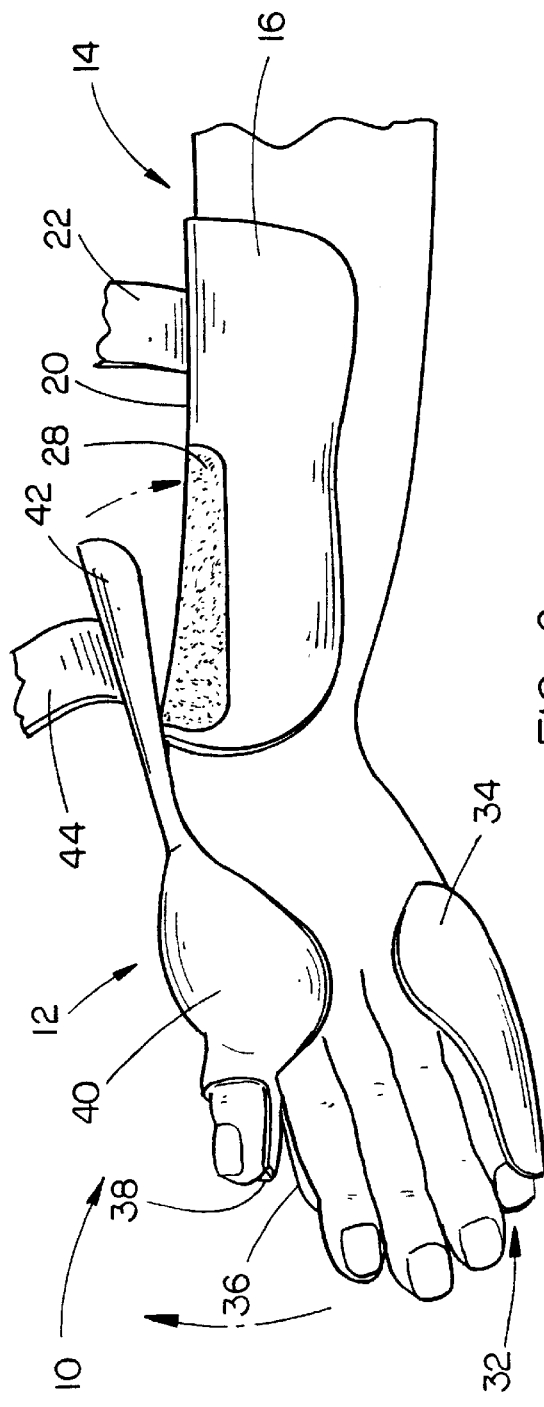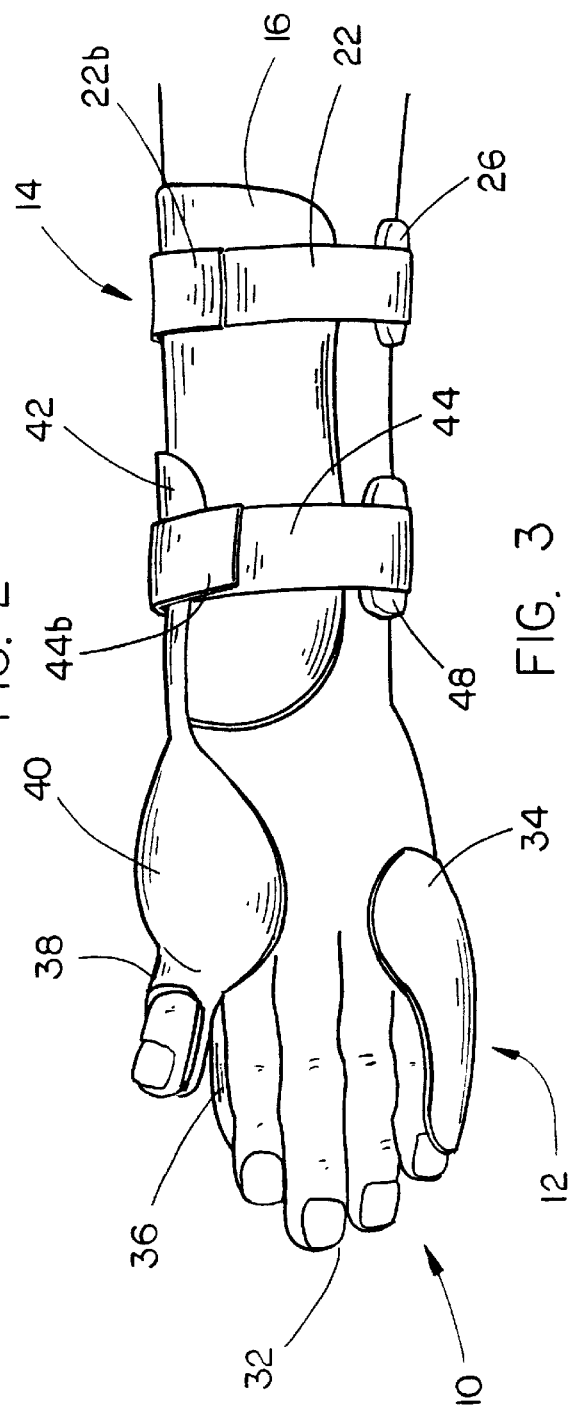

TWO PIECE WRIST-HAND-FINGER ORTHOSIS

CROSS-REFERENCES TO RELATED APPLICATIONS (Not applicable)

STATEMENT AS TO RIGHTS TO INVENTIONS MADE UNDER FEDERALLY SPONSORED RESEARCH AND DEVELOPMENT (Not applicable)

BACKGROUND OF THE INVENTION (1) Field of the Invention

The present invention relates generally to the field of contracture management orthotics, and more particularly to an improved two-piece orthotic device permitting more accurate casting of the extremity, and facilitating the simple, effective, and quick application of the device to a patient.

(2) Background Information

There are three general options available for splints for individuals with non-rigid contractures. First, over the counter (OTC) splints are available and are pre-sized from extra small through extra large, for left or right limbs. Second, a custom-made low temperature plastic splint is also currently utilized in the art, and is fabricated directly on the patient. Finally, a custom splint may be fabricated from a negative casting of the affected extremity.

Over the counter splints are economically manufactured because they are pre-sized. However, such splints do not typically fit the user very well without some modification or customization. This is typically accomplished by "spot heating" the splint with a heat gun and then remolding the splint as necessary to conform to the patient's extremity. The splint is then backfilled with padding. The finished product is most often not aesthetically pleasing. Depending upon the skill of the technician, the splint can also be uncomfortable because of the rough areas where modifications have been made to the splint.

Custom splints formed directly on patients are made of low temperature plastic and often share the same problems as the OTC splints. In addition, when forming the splint on a patient having a non-rigid contracture, it is necessary to hold the hand and wrist in a neutral or other predetermined position while such splints are being molded. This task can be very difficult since the patient is unable to assist in maintaining the predetermined orientation of the extremity. Moreover, low temperature plastic is a relatively soft material, and therefore does not hold up well over time.

Custom splints made from a negative casting of the patient's affected extremity are known to be made using high temperature plastics. These are more rigid and durable than low temperature plastics and will usually last several years. While such custom splints have the potential of providing a durable product with the best possible fit, the practitioner must often struggle with the problem of casting across one or more joints affected by spasticity with high levels of tone. Trying to cast the extremity in a neutral or other predetermined alignment while struggling to hold the hand, wrist and forearm in this alignment, can be very difficult. Creating the necessary negative cast typically requires the use of two hands and a very tight grip just to align the patient's extremities. Often, It can take several minutes to gradually obtain the desired position of the hand and wrist. If the extremities are released in order to wrap the casting material around the patient's hand and wrist, the desired position is immediately lost. Repositioning the hand and wrist after applying the casting material distorts the negative cast. The distortion occurs because the casting material is stretched out of shape and thereby loses the desired "total contact" of the negative cast. The shape of the cast and therefore the resulting splint is also distorted by the practitioner's grip in trying to regain control of the patients wrist and hand and place them into a neutral or other predetermined position.

In addition to providing a less than optimal fit, a common problem of all three prior art types of splints is in the donning of the splint by the patient. As mentioned above, it can take several minutes for a trained occupational therapist or orthotist to manipulate the hand and wrist of a patient with a very tight wrist flexion contracture into a neutral or predetermined position. The average care giver in a skilled nursing facility, rehab hospital, or other group home typically has neither the time, training nor skill required to properly apply a straight, rigid splint on such a contracture. Thus, many patients who could benefit from such a device either go without them, or are poorly positioned in the splint, and therefore do not receive the full benefit of the device.

BRIEF SUMMARY OF THE INVENTION

Difficulties of prior art orthotic techniques and design are alleviated by utilizing the better fitting and more easily donned wrist splint disclosed within.

Therefore, it is a general object of the present invention to provide an improved two-piece wrist-hand-finger orthosis (WHFO) and method of casting the same.

Another object of the present invention is to provide a two-piece orthosis with a lever, to assist in donning the splint on the patient's extremity.

A further object is to provide an improved casting technique for producing a nearly unresisted casting of the affected extremity.

These and other objects of the present invention will be apparent to those skilled in the art.

The two-piece wrist-hand-finger orthosis of the present invention includes a rigid forearm section secured to the patient's arm, and a rigid hand section with a proximally projecting extension lever. The hand section is donned on the patient with the patient's hand in flexion. The hand section is then leveraged into neutral by pivoting the extension lever downwardly into contact with the forearm section. The extension lever is then secured to the forearm section.

BRIEF DESCRIPTION OF THE SEVERAL VIEWS OF THE DRAWING

The preferred embodiment of the invention is illustrated in the accompanying drawings, in which similar or corresponding parts are identified with the same reference numeral throughout the several views, and in which:

FIG. 2 is a top plan view of the orthosis with the forearm and hand sections on the patient, prior to correction of the deviation; and FIG. 3 is a view similar to FIG. 2, but with the deviation corrected and the hand section secured to the forearm section.

DETAILED DESCRIPTION OF THE INVENTION

Figure 1:
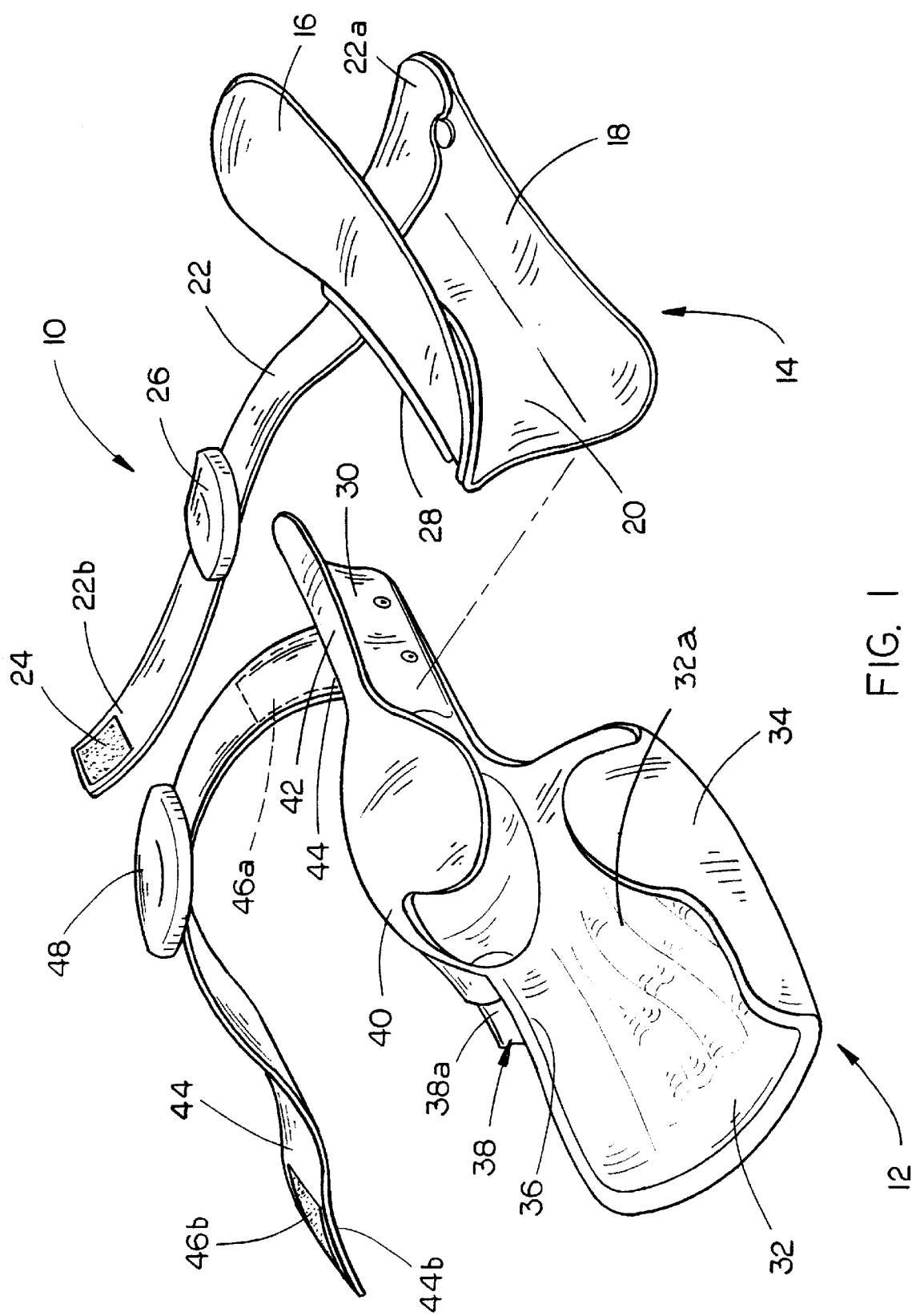
FIG. 1 is a perspective view of the invention prior to attachment to a hand/wrist of a patient.

Referring now to the drawings, the two-piece WHFO of the present invention is designated generally at 10 and includes a hand section 12 and a forearm section 14 which are detachably interconnected to form the splint.

Forearm section 14 is a vacuum-formed rigid plastic unit formed in the shape of a channel open along the ulnar side to permit insertion of the forearm of the patient. Forearm section 14 includes a dorsal leg 16, a palmer leg 18, and a radial back 20 connecting 16 and 18. Because hand section 12 and forearm section 14 are formed based upon a negative casting of the patient's arm, forearm section 14 will have a snug full-contact fit on the patient's forearm.

A securement strap 22 has a first end 22a affixed to the external face of palmer leg 18, and a length to extend completely around the back 20, dorsal leg 16, and ulnar surface of the patient's forearm, and back over the top of the first end 22a. The second end 22b of strap 22 has one-half of a hook and loop fastener material 24 thereon, to permit selectively removable attachment to the corresponding half of the hook and loop fastener material on the external face of first end 22a. Padding 26 is mounted on the inward face of strap 22 generally midway between ends 22a and 22b, so as to contact the patient's arm in the ulnar opening in forearm section 14.

Strap 22 is preferably mounted at the proximal end 14a of forearm section 14, with the remainder of forearm section 14 extending distally along the patient's arm towards the patient's wrist. A patch of hook and loop fastener material 28 is mounted on the outward face of back 20 generally from the distal end 14b proximally towards proximal end 14a. Hook and loop fastener patch 28 is located to selectively engage a corresponding hook and loop fastener patch 30 on hand section 12 to selectively secure hand section 12 to forearm section 14.

Referring now to FIG. 1, hand section 12 is also a vacuum-formed piece of rigid plastic. Hand section 12 may have a hollow, tubular, elliptical shape, with the patient's hand journaled therethrough and supported on a base portion 32. In the alternative, the tubular piece may be trimmed to form a generally C-shaped channel open along the upper end to permit insertion of the wrist and hand directly on to base portion 32. This C-shaped embodiment is shown and described herein. Base portion 32 has a width designed to support the four fingers of the patient's hand. A first wall 34 projects upwardly from the ulnar edge of base portion 32 and curves partially over the dorsal surface of the fingers. A ridge 36 projects slightly upward between the thumb and forefinger, to form a cushioned surface for the forefinger of the hand.

A separate thumb support channel 38 extends radially outward from ridge 36, to support the patient's thumb therein. Ridge 36 forms a load point against the thenar eminence and lateral side of the thumb, with the thenar eminence taking most of the load. The upper surface 32a is arched upwardly, so that the hand is supported with a palmer arch, with the phalangeal joints at an optimal amount of either flexion or extension for the deviation (in the drawings the upper surface is arched to support the phalangeal joints at approximately 20°–30° of flexion), and the thumb slightly abducted. The walls of the thumb support channel 38 would extend upwardly to a point at least flush with the top of the thumb, to securely hold the thumb in position. The radial wall 38a flows into the radial wall 40 of hand section 12.

An extension lever 42 extends proximally from radial wall 40 and extends a distance to overlap the radial back 20 of forearm section 14. As discussed above, hook and loop fastener patch 30 is mounted on the inward face of lever 42, for selective securement to the hook and loop fastener patch 28 on forearm section 14. Extension lever 42 is specifically located on hand section 12 at a location that is opposite the extremity deviation to be corrected in the patient. The majority of deviations to be corrected are ulnar deviations, so that lever 42 is most frequently located on the radial side of hand section 12. As discussed in more detail hereinbelow, the location of lever 42 assists in aligning the patient's hand in the neutral position.

As shown in FIGS. 1–3, a securement strap 44 has a first end secured to the outward face of lever 42, and has a length to extend around the dorsal leg 16, the patient's exposed forearm in the forearm section 14, the forearm section palmer leg 18, and thence overlapping the first end 44a. Corresponding hook and loop fastener patches 46a and 46b on the outward face of the first end 44a and inward face of the second end 44b of strap 44 secures the strap into position. Padding 48 is located midway between the ends of strap 44, where the strap would be secured against the patient's forearm.

In use, it can be seen that even personnel with little training will be able to quickly and effectively apply the WHFO to a patient with non-rigid contractures of the hand and wrist. First, the forearm section 14 is secured to the forearm of the patient with the radial back 28 in contact with the radial side of the forearm, and the distal end 14b proximal the wrist crease. Strap 22 is then secured around the proximal end of forearm section 14 of the patient's forearm, to secure the forearm section into position.

The hand section is then applied to the hand of the patient, with the patient's thumb journaled in the thumb support channel 38, and the patient's fingers resting on base portion 32. Because the patient's hand is in a natural position with the wrist in flexion, the hand section 12 is more easily applied to the patient's hand. The patient's hand and wrist are then moved to a neutral or other predetermined alignment by lifting upward on the base portion 32 while pushing down on lever 42. The mechanical advantage provided by lever 42 allows the hands to be easily moved to the desired alignment. The hook and loop fastener patches 30 and 28 hold the hand section 12 in alignment with forearm section 14, and securement strap 44 is then wrapped around the forearm section 14 and patient's forearm to maintain the hand section 12 in this position. This two-piece approach to the WHFO allows proper donning of the hand section without resistance, because the patient's wrist is allowed to be in flexion during donning of the device.

The inventor herein has also devised a two stage casting technique to produce the two-piece WHFO. This two stage technique employs either a pre-sized or custom made casting plate and allows for nearly unresisted casting. By casting the hand section separately, with the wrist in flexion, the method is more efficient than those of prior art and results in a better fitting orthotic device.

The preferred practice of this method begins with determining the range of motion (ROM) of the patient. This information is used to understand the general shape of the orthotic which will result in optimal correction.

To facilitate the negative casting procedure, a casting plate is first molded to maintain the hand/palm and thumb in a neutral position. Custom molding of this type is well known in the art. The casting plate is designed to support the hand in a "resting" position that is more easily achieved with the wrist flexed so as to reduce the resistance of tight flexors or tone. The phalangeal joints should be at an optimal amount of flexion or extension for the particular deviation, with the thumb slightly abducted. Casting plates may be made which facilitate their connection to the patient and aid in manipulation of the extremity.

Once the casting plate has been created, the plate is placed under the patient's hand to support the hand in the "rest" position. Two layers of a snug-fitting casting stockinette are then applied to the forearm, wrist and hand. Preferably, the stockinette extends from two inches proximal the elbow to two inches distal the fingertips. A casting strip is affixed to the ulnar side of the forearm with thin medical tape, allowing enough of the strip to extend distally to incorporate into the hand section. With the wrist still in flexion, a couple of layers of casting material are applied to the forearm. This should be a thin layer of fiberglass or plaster, to decrease the difficulty of removal. While the forearm casting is setting, the wrist should be leveraged to neutral or the desired predetermined position by placing a thumb in the arch of the casting plate and one or two fingers on the back of the wrist. The patient's wrist is then leveraged to the desired position with the casting plate maintaining the hand in the correct position. Once optimal alignment of the wrist is achieved, casting material is applied to the hand and incorporated with the forearm section. When the casting material has completely set, it should be removed in one piece, with the casting plate mounted to the casting on the interior of the stockinette.

All standard measurements are then taken, including pertinent width, circumferential and length measurements; finger tips to MCPs; MCPs to wrist; wrist to cubital crease; width at MCP and wrist; circumference of MCPs, wrist and proximal two-thirds of forearm.

The negative cast is then filled with plaster to form a positive mold. The negative cast is removed and the positive mold is modified in the usual manner. Padding is then added to areas of anticipated pressure, including: proximal/volar forearm; dorsal wrist; ulnar surface of hand section extending superiorly across the dorsal aspect of the hand between the MCP joint and wrist and extending into the dorsal wrist padding.

Once the positive mold is completed, with padding, the forearm section of the WHFO is vacuum-formed. It is then removed and trimmed and placed back onto the positive mold. The hand section is then vacuum-formed, extending over the forearm section. The hand section is removed and trimmed. The straps and fastener materials are then added to the hand section and forearm sections to complete the WHFO.

Whereas the invention has been shown and described in connection with the preferred embodiment thereof, many modifications, substitutions and additions may be made which are within the intended broad scope of the appended claims. For example, the preferred embodiment of the hand section 12 has an open portion over the dorsal surface of the fingers of the hand. This is not absolutely necessary, and the hand could be journaled through a hand section with a closed back, or a thumb channel with a closed back. Similarly, other types of fasteners and materials could be used to connect the hand section to the forearm section, and to attach the forearm section to the forearm of the patient.

I claim:

1. A two-piece orthosis, comprising:
   a generally rigid limb section adapted for selective, removable securement to a user's limb, proximal to the user's deviated extremity;
   a generally rigid extremity section adapted for selective, removable securement to the user's deviated extremity;
   said extremity section including a generally rigid extension lever having a first half of a cooperable fastener thereon, and the limb section including a second half of the cooperable fastener thereon, said first and second cooperable halves operable to selectively fasten the extremity section to the limb section with the extremity and associated joint between the extremity and limb in a substantially neutral orientation; and
   said extension lever located on the extremity section in an orientation projecting opposite a deviation to be corrected and extending a distance to overlap the limb section,
   whereby said overlap of the extension lever is sufficient to provide the sole means for both fastening the extremity section to the limb section and selecting said substantially neutral orientation.

2. A two-piece orthosis, comprising:
   a generally rigid forearm section adapted for selective, removable securement to a user's forearm;
   a generally rigid hand section adapted for selective, removable securement to the user's hand;
   the hand section including an-a generally rigid extension having a first half of a cooperable fastener thereon, and the forearm section including a second half of the cooperable fastener thereon, said first and second cooperable halves operable to selectively fasten the hand section to the forearm section with the hand and wrist in a substantially neutral orientation; and
   the extension lever located on the hand section in an orientation projecting opposite a hand/wrist deviation to be corrected in the user and extending a distance to overlap the forearm section,
   whereby said overlap of the extension lever is sufficient to provide the sole means for both fastening the hand section to the forearm section and selecting said substantially neutral orientation.

3. The two-piece orthosis of claim 2, wherein said forearm section has a generally C-shaped cross-section, with a dorsal leg, a palmer leg and a radial back.

4. The two-piece orthosis of claim 2, wherein said hand section includes a base portion adapted to support four fingers of the user's hand, and a thumb support channel mounted to a radial edge of a palmer surface of the base portion, and further including a ridge projecting slightly upward from the radial edge of the base portion.

5. The two-piece orthosis of claim 4, wherein the base portion has an upper surface arched upwardly to support the hand.

6. The two-piece orthosis of claim 5, wherein the base portion dorsal surface is arched superiorly a distance to support the phalangeal joints at a predetermined amount of flexion.

7. The two-piece orthosis of claim 4, wherein the thumb support channel is oriented to support the thumb in a slightly abducted position.

8. The two-piece orthosis of claim 4, wherein a radial wall of the thumb support channel extends upwardly to form a radial wall of the hand section, further comprising an ulnar wall projecting from an ulnar edge of the base portion, and wherein the ulnar and radial walls project upwardly a distance at least to the dorsal surface of a hand supported in the hand section.

9. The two-piece orthosis of claim 8, wherein the deviation to be corrected is an ulnar deviation, and wherein the extension lever extends proximally from the radial wall of the hand section.

10. The two-piece orthosis of claim 9, wherein said hand section is open between the ulnar and radial walls to permit insertion of the hand into the hand section.

11. The two-piece orthosis of claim 3, further comprising a securement strap attached at a first end to one leg of the forearm section, said strap having a length sufficient to wrap around the forearm section and the user's forearm with a second end of the strap overlapping the strap, and including a fastener means for releasably fastening the second end of the strap to a portion of the strap.

12. The two-piece orthosis of claim 11, further comprising a second securement strap attached at a first end to the extension lever, said strap having a length sufficient to wrap around the forearm section and the user's forearm with a second end of the strap overlapping the second strap, and including a fastener means for releasably fastening the second end of the second strap to a portion of the second strap.

13. A method for donning the two-piece orthosis of claim 11 comprising:
   a) securing the forearm section to the forearm of the user;
   b) inserting the user's hand into the hand section with the user's wrist in flexion;
   c) pivoting the user's hand into a neutral position by moving the extension arm towards the forearm section; and
   d) securing the extension lever to the forearm section with the wrist in the neutral position.

14. A method for donning a two-piece orthosis of the type having a forearm section and a hand section; the hand section having an generally rigid extension lever rigidly attached to said hand section such that movement of said lever results in substantially the same angle of movement in the user's hand, comprising the steps of:
   a) securing the forearm section to the forearm of the user;
   b) inserting the user's hand into the hand section with the user's wrist in flexion;
   c) pivoting the user's hand into a neutral position by moving the extension lever towards the forearm section; and
   d) securing the extension lever to the forearm section with the wrist in the neutral positions,
whereby securing the extension lever to the forearm section is sufficient to provide the sole means of both fastening the hand section to the forearm section and selecting said neutral position.

15. A method for donning a two piece orthosis of the type having a limb section and a generally rigid extremity section, said extremity section being capable of connecting to a user with little or no play, said extremity section having a generally rigid extension lever projecting in the general direction of said limb section, comprising the steps of:
   a) securing the limb section to the limb of said user;
   b) inserting the user's extremity into the extremity section with the user's joint between the extremity and limb in a substantially deviated orientation;
   c) pivoting the users extremity into a neutral position by moving the extension lever towards the limb section; and
   d) securing the extension lever to the limb section with the extremity and limb in a substantially neutral position,
whereby securing the extension lever to the limb section is sufficient to provide the sole means of both fastening the extremity section to the limb section and selecting said neutral position.

16. A method for donning a two-piece orthosis of the type having a generally rigid limb section and a generally rigid extremity section, said extremity section being capable of connecting to a user with little or no play, said extremity section having a generally rigid extension lever projecting in the general direction of said limb section, comprising the steps of:
   a) securing the limb section to the limb of said user;
   b) inserting the user's extremity into the extremity section with the user's joint between the extremity and limb in a substantially deviated orientation;
   c) pivoting the user's extremity into a neutral position by moving the extension lever towards the limb section; and
   d) securing the extension lever to the limb section with the extremity and limb in a substantially neutral position,
whereby securing the extension lever to the limb section is sufficient to provide the sole means for both fastening the extremity section to the limb section and selecting said substantially neutral orientation.

17. A method for donning a two-piece orthosis of the type having a generally rigid forearm section and a generally rigid hand section, said hand section being capable of connecting to a user with little or no play, said hand section having a generally rigid extension lever projecting in the general direction of said forearm section, comprising the steps of:
   a) securing the forearm section to the forearm of said user;
   b) inserting the user's hand into the hand section with the user's joint between the hand and forearm in a substantially deviated orientation;
   c) pivoting the users hand into a neutral position by moving the extension lever towards the forearm section; and
   d) securing the extension lever to the forearm section with the hand and forearm in a substantially neutral position,
whereby securing the extension lever to the forearm section is sufficient to provide the sole means for both fastening the hand section to the forearm section and selecting said substantially neutral orientation.

* * * * *